US006421414B1

(12) United States Patent
Huber

(10) Patent No.: US 6,421,414 B1
(45) Date of Patent: Jul. 16, 2002

(54) DETECTOR FOR LARGE WAFER SURFACES

(75) Inventor: Anton Huber, Holzkirchen (DE)

(73) Assignee: GeMeTec Gesellschaft fuer Messtechnik und Technologie mbH, Munich (DE)

( * ) Notice: Subject to any disclaimer, the term of this patent is extended or adjusted under 35 U.S.C. 154(b) by 0 days.

(21) Appl. No.: 09/684,056

(22) Filed: Oct. 6, 2000

(30) Foreign Application Priority Data

Oct. 7, 1999 (DE) .......................................... 199 48 382

(51) Int. Cl.⁷ .......................................... G01N 23/223
(52) U.S. Cl. .............................. 378/45; 378/84; 378/85
(58) Field of Search .............................. 378/44, 45, 85, 378/82, 84; 250/370.13

(56) References Cited

U.S. PATENT DOCUMENTS 5,732,120 A  3/1998  Shoji ........................... 378/45

FOREIGN PATENT DOCUMENTS

| DE | 4130556  | 3/1993  |
| DE | 19546142 | 6/1997  |
| DE | 19620081 | 11/1997 |

OTHER PUBLICATIONS

Schwenke, H., Beaven, P.A., Knoth, J., "Applications of Total Reflection X-ray Fluorescence Spectrometry in Trace Element and Surface Analysis", Fresenius J Anal Chem (1999) 365:19–27, Jan. 17, 2002.

Tragbares Minilabor, TR. Technische Rundschau Nr. 47/48 (1997), Jan. 17, 2002.

*Primary Examiner*—David V. Bruce
*Assistant Examiner*—Therese Barber
(74) *Attorney, Agent, or Firm*—Dilworth & Barrese, LLP

(57) ABSTRACT

The invention relates to an apparatus for total reflection X-ray fluorescence analysis, which allows a faster and more precise detection of the X-ray fluorescence spectrums of a sample. DRIFT detectors are used in the transducer of the apparatus in which charge carriers created can be accelerated towards a collecting anode of a very small design by a radial component of the electrical field generated by annular electrodes. A faster and more precise measurement of the charge carriers generated in the detector interior is possible due to the low capacitance of the collecting anode. The X-ray fluorescence of a sample can be measured in high-sensitive resolution by an array comprising such DRIFT detectors. The surface concentrations of the different foreign atoms in the sample can be determined in high-sensitivity resolution from the X-ray fluorescence spectrums obtained.

28 Claims, 7 Drawing Sheets

DETECTOR FOR LARGE WAFER SURFACES

BACKGROUND OF THE INVENTION

The invention relates to an apparatus for the total reflection X-ray fluorescence analysis (TRFA) in which the smooth planar surface of a sample or thin film on a sample is excited by the incident X-ray radiation and the X-ray fluorescence radiation emitted is detected spectrally and which comprises a radiation source, a monochromator and a transducer. The invention further relates to the use of such an apparatus for the determination of foreign atom concentrations on wafer surfaces and to a method for the high-sensitivity resolution measurement of foreign atom concentrations on a wafer.

In total reflection X-ray fluorescence analysis, the surface of a sample is exposed at a very flat angle of incidence to the X-ray radiation generated by an X-ray tube. The angle of incidence is selected so that the incident X-ray is totally reflected. The total reflection geometry means that there is only a certain radiation intensity in a near-surface layer of around 3 nm thickness. For this reason, only the atoms of this thin surface area is excited by the incident X-ray radiation. The excited atoms emit fluorescent X-ray quanta of a certain energy which are characteristic for the relevant atom. The energy spectrum emitted by all surface atoms is measured using a detector and the concentration of an element in the thin surface film can be determined from the intensity of the peak associated with the respective element.

Germanium or silicon detector (Si(Li)) are used to register the energy spectrum with the apparatus for X-ray fluorescence analysis used up to now. All these detectors utilize the fact that the incident X-ray quanta have a very strong ionizing effect and so generate a plurality of charge carriers in the semi-conductor material. The higher the energy of the X-ray quantum, the more charge carriers are generated. The charge quantities generated in the detector are therefore measured at periodic intervals and transduced into an energy spectrum by means of a multi-channel analyzer to read out the detector. Counts of up to $2-10^4$ counts per second (cps) can be achieved with such detectors; $2-10^4$ X-ray quanta per second can therefore be measured.

One disadvantage of such detectors is that they only supply high-resolution energy spectrums when the thermal noise is effectively suppressed by cooling with liquid nitrogen. The required nitrogen Dewar flasks are large and problematic to handle.

German Patent DE196 20 081 A1 and PCT application PCT/DE97/01015 describe a strip detector and a method of manufacturing a strip detector for the detection of ionizing particles and/or radiation. Regions n-doped at least at one substrate surface of the silicone substrate and a p-doped insulation region between the n-doped regions are provided as strips and voltage supply areas. A first insulator film is applied to one substrate surface and metal strips are arranged above the n-doped region.

SUMMARY OF THE INVENTION

The invention is characterized by at least one further insulation film being provided immediately above the first insulator film and by at least one of the insulation films being interrupted in projection over the intermediate region of two adjacent n-doped regions and by the p-doped insulation area having a lateral p-dope material concentration distribution which provides a higher dope material concentration in the region beneath the interruption of the interrupted insulation film than in the insulation region directly adjacent to the n-doped region. The insulation structure in accordance with the invention is also suitable for the insulation of guard rings which gradually reduce the high operating voltage towards the detector periphery. It insulates adjacent rings extending around the whole detector so that different potentials with low electrical field strengths can develop on them.

It is the object of the invention to provide an apparatus and a method for X-ray fluorescence analysis to allow a faster measurement with better resolution of the X-ray fluorescence of a sample and a reduction in the effort required to cool the detector.

This object is solved in accordance with the invention by an apparatus for total reflection X-ray fluorescence analysis in which the smooth planar surface of a sample or thin film on a sample is excited by the incident X-ray radiation and the X-ray fluorescence radiation emitted is detected spectrally and which comprises a radiation source, a monochromator and a transducer, with the transducer comprising at least one DRIFT detector, an electrical field being capable of generation in each DRIFT detector by means of an electrode array of electrodes at different voltage levels and having a radial component. Charge carriers which are created are accelerated towards a low-capacitance collecting electrode by this radial component of the electrical field.

Counts of up to $10^5$ cps can be achieved by using a transducer with at least one DRIFT detector. This is made possible by the charge carriers generated by an X-ray quantum being guided faster to the collecting electrode through the electrical field prevailing in the detector interior. The main reason for the high count capable of being achieved with the aid of DRIFT detectors is, however, the low capacitance of the collecting electrode. The radial component of the electrical field accelerates the charge carriers towards the collecting electrode and as a result the collecting electrode can be made with a small surface and so a low capacitance.

In summary it can be said that the read-out times can be shortened significantly when DRIFT detectors are used. Higher counts can be processed in this way and spectrums with better energy resolution are obtained. DRIFT detectors also require less effort for cooling; in particular, the high-effort nitrogen cooling can be omitted.

It is of advantage if the electrode array comprises a plurality of annular electrodes arranged concentrically and at different voltage levels. With such an electrode array, an electrical field with a radial component is produced.

In accordance with another advantageous embodiment of the invention, a first transistor of a pulse amplification stage is integrated in the collecting electrode. This can be done by the film structures of a field-effect transistor being integrated in the centre of the DRIFT detector, the gate of the field-effect transistor being electrically connected to the collecting electrode. In this way, the connection between the collecting electrode and the gate of the FET can be shortened and the parasitic capacitance of the connecting line is greatly reduced. Moreover, there is a reduction in the noise captured by the inductive coupling.

In accordance with another aspect of the invention, the DRIFT detector can be cooled by means of a Peltier cooler element. A cooling of up to 30° relative ambient can be achieved with a one-stage Peltier cooler element. Such a cooling is sufficient to allow highly resolved energy spectrums to be registered by DRIFT detectors. The nitrogen cooling required for prior detectors can therefore be replaced by a Peltier cooler, with the Peltier element being integrated directly in the DRIFT detector.

It is of advantage to arrange the radiation source, the monochromator and the transducer in a vacuum housing. Moreover, it is of advantage if the transducer has a thin window of a thickness of less than 2 μm as the measurement window. It is furthermore of advantage if the radiation source consists of a low energy X-ray tube.

The measurement range of total reflection X-ray fluorescence analysis can be expanded to elements with a low ordinal number Z, that is to light elements, using the three above-mentioned measures. These elements emit fluorescence X-ray radiation of only low energy. The unwanted absorption values of the X-ray radiation can be reduced with the aid of the vacuum housing and of the thin measurement window. A low-energy X-ray tube emits excitement radiation which is near the energy of the fluorescent X-ray radiation of light elements. The fluorescence efficiency can be increased in this way.

It is of advantage to arrange a sample table opposite the transducer to accommodate a sample, with the sample table being made longitudinally displaceable preferably in the z direction and the x,y direction, rotatable around its middle axis and pivotable in a circle segment guide.

In total reflection X-ray fluorescence analysis, the angle of incidence has to be set precisely to 0.1 to 0.2 arc minutes. This can be done using an adjustable precision sample table.

It is furthermore of advantage when the sample table has a suction plate as the accommodation plate in which a plurality of pints are integrated which can be travelled above its upper plane. With the help of the suction plate, the sample, for example a wafer, can be sucked in the direction of the sample table. A more precise guide and a more exact positioning of the sample can be achieved in this way. To detach the sample or wafer from the plate again, pins provided for this purpose are travelled out. The sample or wafer can then be removed, for example, by a robot grabber.

In accordance with another advantageous embodiment of the invention, a scattered radiation diaphragm is positioned in front of the transducer. Such a scattered radiation diaphragm prevents scattered X-ray radiation from becoming incident on the transducer by the scattered radiation being absorbed by the diaphragm.

It is of advantage here if the scattered radiation diaphragm can be travelled in a z direction, for in this way, an adaptation of the position of the scattered radiation diaphragm to the thickness of the sample measured in each case can be carried out.

In accordance with another advantageous aspect of the invention, the excitation of the sample occurs by means of an incident parallel X-ray which is generated with the aid of parabolically arranged Bragg reflectors which reflect the X-ray radiation generated by the X-ray tube. Exactly as with a parabolic mirror, it is possible with this arrangement of Bragg reflectors to form a parallel X-ray from the divergent radiation generated by the X-ray tube. By the X-rays emitted in different directions being capable of bundling into one ray, an excitation ray of high intensity can be provided. Either crystals or multi-layer systems can be used as the Bragg reflectors.

In accordance with another advantageous embodiment of the invention, the transducer has a detector array of a plurality of DRIFT detectors which allows the high-sensitivity resolution recording of the X-ray fluorescence radiation of the sample. A statement can be made on the distribution of the different elements on the sample surface by means of such an array of DRIFT detectors. For this purpose, each of the DRIFT detectors may only detect the fluorescence radiation from a defined small region of the sample. A low fluorescence intensity can be utilised better with the aid of DRIFT detectors than with conventional detectors and good energy spectrums are achieved despite the low fluorescence intensity. Only in this way is it possible to achieve a high-sensitivity resolution recording.

However, for this purpose, it is necessary for each DRIFT detector to have its own pulse amplification chain. It can be expected that in the near future integrated circuits will be available in which the required pulse amplification electronics is integrated.

When an array of DRIFT detectors is used, it is of advantage if the detector array can be operated in a first and a second mode, with the X-ray fluorescence radiation of the probe being measured at high-sensitivity resolution in the first mode and the sum spectrum of the X-ray fluorescence spectrums supplied by the individual detectors being determined in the second mode.

While the high-sensitivity resolution measurement allows a statement on the distribution of the elements on the surface measured, the sum spectrum allows a lower resolution limit because a substantially higher number of fluorescence X-ray quanta was taken into account in the calculation of the sum spectrum. The evaluation of the sum spectrum allows a statement on the mean concentrations of foreign atoms on the sample or wafer surface.

In accordance with another advantageous aspect of the invention, the sample and the transducer can be moved relative to one another in the x,y direction. Here, the transducer comprises a detector array of a plurality of DRIFT detectors. It is possible in this way to detect the foreign atom concentrations of a wide-area sample, in particular of a wafer, with a detector array only covering a part of the wafer surface. Here, the detector can be moved over the stationary sample, on the one hand, and a stationary detector array can be provided, on the other hand, under which the sample is moved. A third possibility is to move both the detector and the sample.

With regard to a high-sensitivity resolution recording of the X-ray fluorescence radiation, it is in particular of advantage in the measurement of circular samples to make the detector array in the form of at least one circle detector, with the detector array and sample being pivoted relative to one another with respect to an axis extending through the sector tip. The detector array consisting of a plurality of DRIFT detectors therefore covers at least one sector in each case of the circular sample or wafer to be measured and a high-sensitivity resolution detection of the fluorescence spectrums is then performed with respect to this part of the sample. Subsequently, the sample or wafer is turned an increment, e.g., one "cake wedge or slice" further relative to the detector to record respective fluorescence spectrums.

When a detector array comprising two diametrically opposed circle sectors is used, the additional advantage of a shorter measuring period results.

In accordance with another advantageous embodiment, the detector array covers an area which is greater than the surface of the sample. In this way, the high-sensitivity resolution recording of the X-ray fluorescence of a sample can be performed with a minimum measuring time.

The apparatus in accordance with the invention for the total reflection X-ray fluorescence analysis can, in particular, be used to determine foreign atom concentrations on wafer surfaces. The silicon wafers used for semi-conductor production are subject to the highest demands for the purity of the silicone used. There are tightly limiting tolerance regions which have to be monitored with regard to foreign atom concentrations. Total reflection X-ray fluorescence analysis is suitable for this purpose in that conclusions with respect to the foreign atom concentrations can be made immediately from the fluorescence spectrums by means of a suitable calibration. The measuring precision can be further increased by the use in accordance with the invention of DRIFT detectors, whereby even very low foreign atom concentrations can be detectable in quantity. A high-sensitivity resolution determination of the foreign atom concentrations on the wafer surface allows a statement on the distribution of different elements on the wafer surface and is therefore of help in being able to find the cause of contaminations. It is important that the apparatus in accordance with the invention for total reflection fluorescence analysis can be integrated in a semi-conductor production line easily and therefore allows a constant quality monitoring.

In the method in accordance with the invention for the high-sensitivity resolution measurement of foreign atom concentrations on a wafer when using a detector array comprising a plurality of detectors, the following steps are performed: first, a relative movement is generated between the detector array and the sample to be measured, wherein the respective local X-ray fluorescence spectrums are transduced. Subsequently, the respective topical foreign atom concentration is calculated from the respective X-ray fluorescence spectrums recorded there.

In this way, the total wafer surface can be checked as regards its content of foreign atoms, with the detector array not having to cover the whole wafer area. The concentrations of foreign atoms at a certain point here result from the size of the peak in the spectrum recorded there. As a result, a high-sensitivity resolution representation of the concentrations of all foreign atoms can be obtained simultaneously with the measurement method described. The method in accordance with the invention for the measurement of the mean foreign atom concentrations on a wafer while using a detector array comprising a plurality of detectors comprises the following steps: first a relative movement is generated between the detector array and the sample to be measured and the relative local X-ray fluorescence spectrums are recorded. Subsequently, the topical X-ray fluorescence spectrums are summed. The mean foreign atom concentrations can then be determined from the sum spectrum obtained in this way.

The concentrations of the foreign atoms result from the peaks in the sum spectrum. The foreign atom concentrations meaned over the wafer surface can be determined with high sensitivity in a short time with the measurement method described.

BRIEF DESCRIPTION OF THE DRAWINGS

Further details and advantages of the invention are described below by way of a number of embodiments represented in the drawings in which.

DESCRIPTION OF THE PREFERRED EMBODIMENTS

Figure 1:
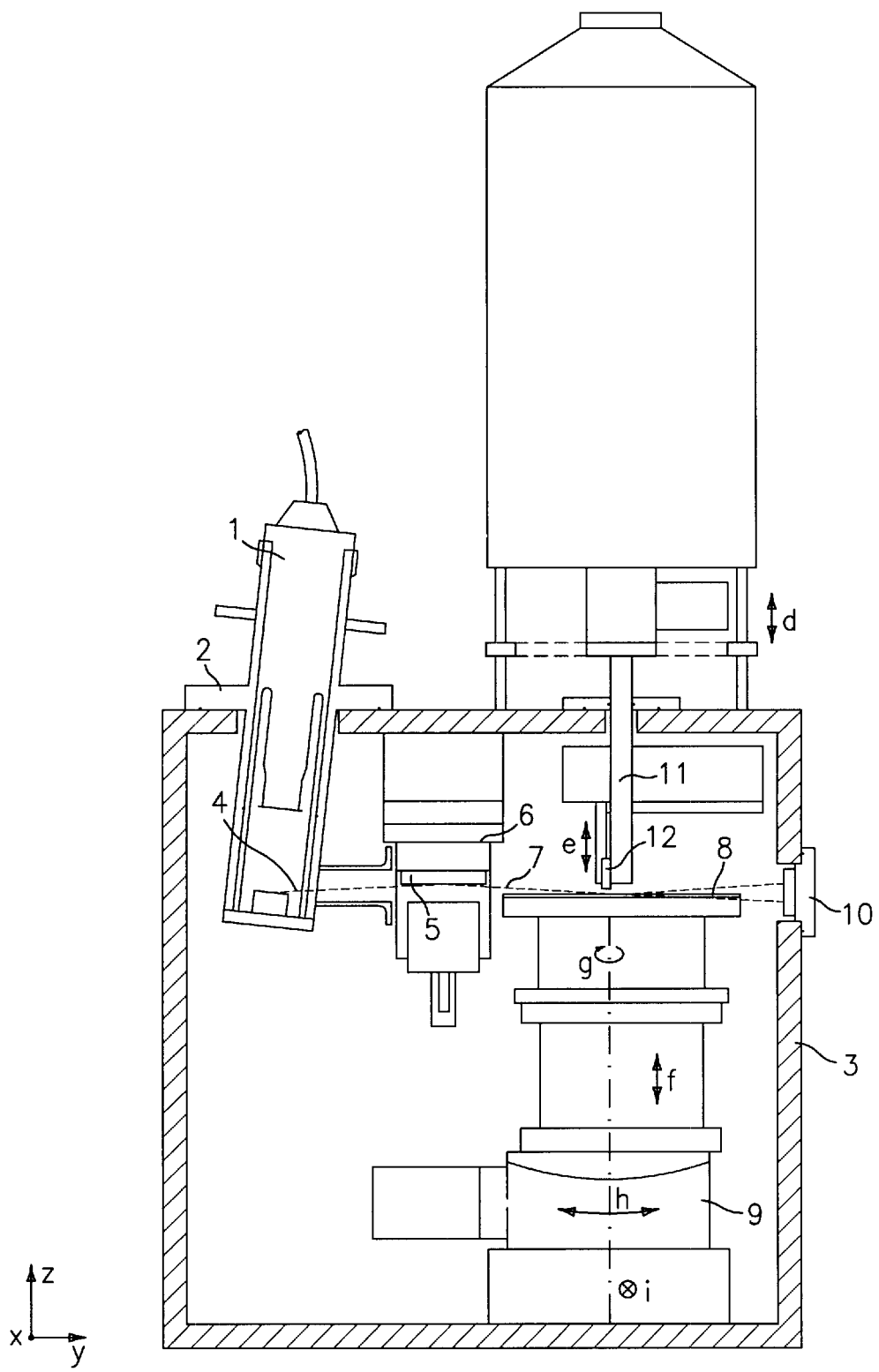
FIG. 1 shows a total representation of an apparatus for total reflection X-ray fluorescence analysis.

In FIG. 1, an apparatus especially suited for total reflection X-ray fluorescence analysis is shown which substantially comprises an X-ray radiation source, a monochromator and a transducer to detect the X-ray fluorescence radiation emitted by the sample. The X-ray tube 1 is fixed in place in the housing 3 by means of the holder 2 so that the picking-off of the X-ray radiation 4 generated can be made at a suitable angle. Chromium, molybdenum, silver, tungsten, etc. can be used as the anode material of the X-ray tube. The X-ray radiation generated is led to a monochromator 5 which can be adjusted relative to the beam path by the holder 6.

A Bragg reflector, which can be either a periodic multi-layer system or a crystal, is used as the monochromator. Bragg reflectors designed as a multi-layer structure have alternating films of a heavy component A (molybdenum, nickel, tungsten, etc.) and films of a light component B (carbon, boron carbide, magnesium, etc.). A certain excitation energy is selected from the energetically broadband X-ray radiation of the X-ray tube by means of the Bragg reflector 5.

The X-ray 7 monochromatized by the Bragg reflector 5 is used for the fluorescence excitation of the sample 8. For this purpose, the X-ray 7 must strike the sample 8 at a very flat angle of incidence which has to be set precisely. The required precision for the setting of the angle of incidence of the primary X-ray radiation is around 0.1 to 0.2 arc minutes. Such a precision can be achieved by using a sample table 9 which is longitudinally displaceable in an x direction (arrow i) and in a z direction (arrow f). Furthermore, the sample table 9 is made rotatably around its central axis (arrow g) and pivotable (arrow h) in a circular segment guide.

So that the sample 8 lying on it can be moved with the precision of the sample table 9, a good connection is required between the sample table and the sample. This connection can be made, for example, using a suction plate or electrostatically by means of a corresponding sample table. A plurality of pins travellable over the upper plane can be integrated in the suction plate or the sample table. In this way, on the one hand, the sample to be examined, for example the wafer, can be securely accommodated. After the measurement, the sample can be raised by travelling out the pins and, for example, taken up by a robot grabber and pulled out laterally through a corresponding aperture in the housing.

To set the right angle of incidence, a reflection detector 10 can be provided in the housing wall and can be used to determine the angle of the X-ray radiation totally reflected from the sample.

The atoms in the surface film of the sample emit their characteristic fluorescence X-ray radiation in all directions after the excitation by the incident X-ray 7. To record the energy spectrum of the fluorescence X-ray radiation, a detector tube 11 is arranged opposite the sample table with the actual transducer being accommodated therein. In the solution in accordance with the invention, the transducer (hidden by the detector tube in FIG. 1) comprises at least one DRIFT detector. The detector tube 11 is opened towards the bottom, that is towards the sample 8, so that the fluorescence radiation emitted can be incident without hindrance. The detector tube 11 can be displaced in the z direction (arrow d) together with the transducer contained therein to allow the measurement geometry to be adapted to the different sample thicknesses.

When the energy spectrums are taken up, scattered radiation should be prevented from reaching the detector. For this purpose, a scattered radiation diaphragm 12 is provided which is also travellable in the z direction.

Figure 2:
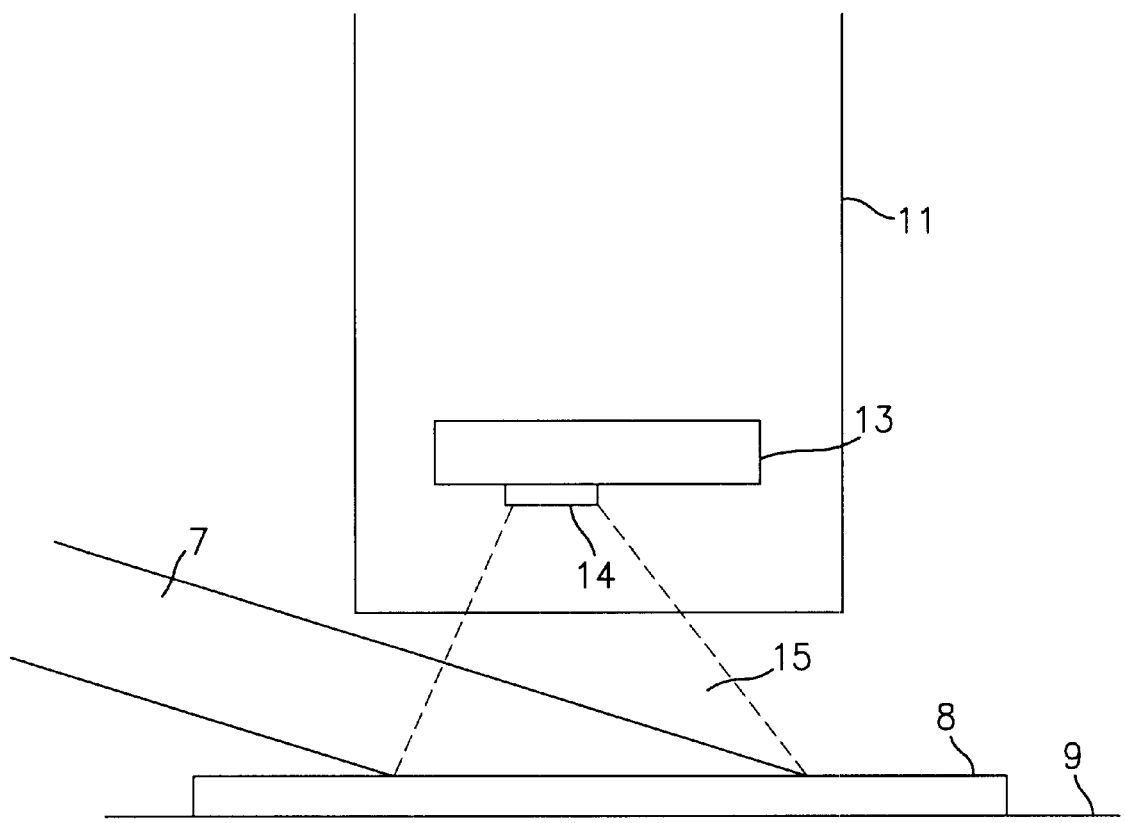
FIG. 2 shows the arrangement of the transducer and the DRIFT detector in the detector tube.

In FIG. 2, the arrangement of the transducer 13 in the detector tube 11 is represented. The transducer 13 comprises at least one DRIFT detector 14 with which the energy spectrum of the fluorescence X-ray radiation 15 emitted by the sample 8 can be taken up. The sample 8 lying on the sample table 9 is exposed to the excitation X-ray 7. The surface atoms of the sample 8 emit fluorescence radiation in all directions, with only the X-ray quanta emitted in the cone 15 being detected by the detector 14.

Figure 3:
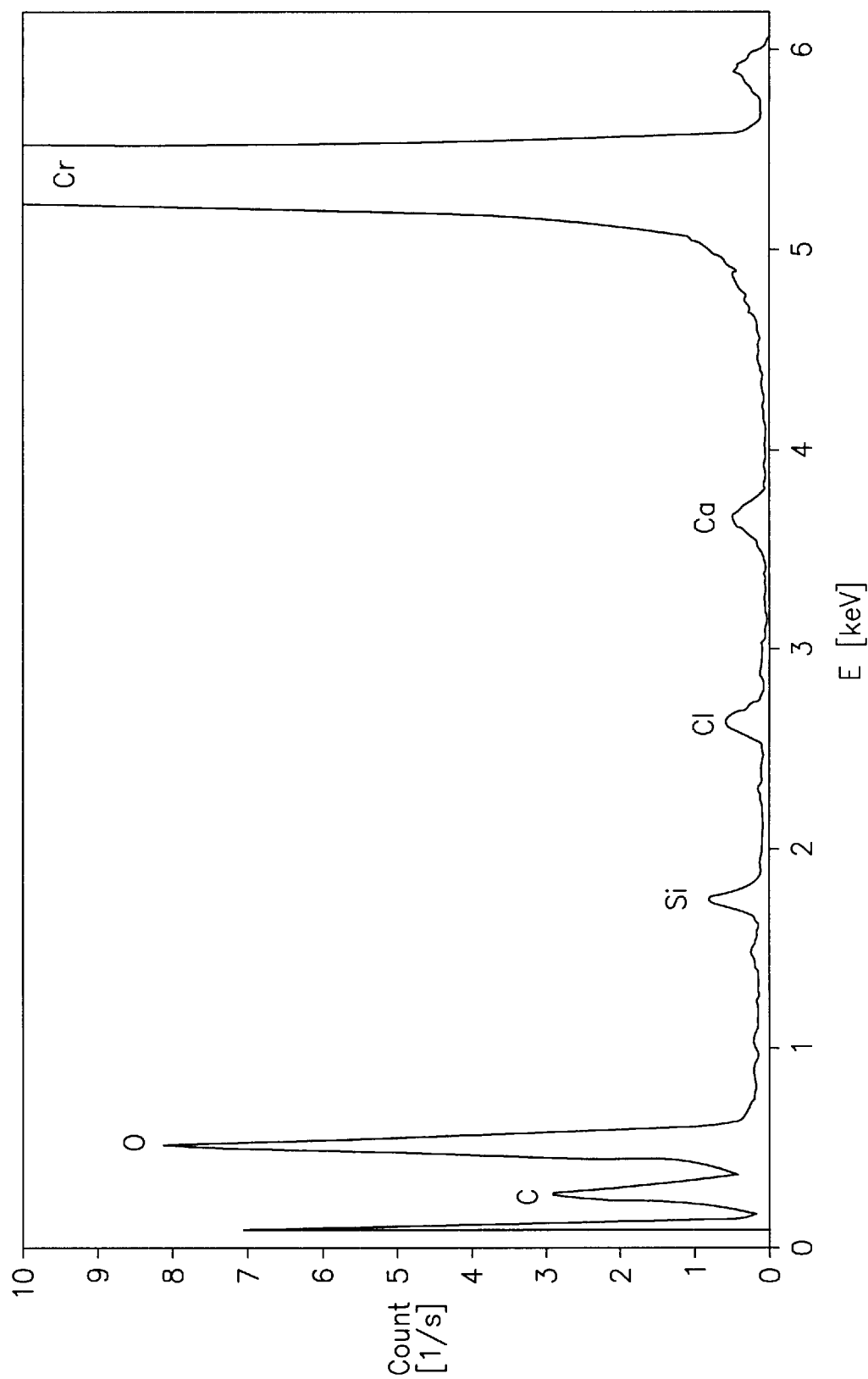
FIG. 3 shows an X-ray fluorescence spectrum taken in the range of low cardinal numbers Z.

FIG. 3 shows a typical fluorescence X-ray spectrum for the range of the lighter elements, that is the elements with a low cardinal number Z. The count (in cps) is shown as a function of the energy of the fluorescence X-ray quanta measured in kilo-electron volt (KEV). Each element (here, for example, C, O, Si, Cl, etc.) contained in the surface film of the sample emits fluorescence radiation of a characteristic energy so that the presence of a certain element can be deduced from the peak in the fluorescence spectrum. With a suitable calibration, a statement can be made on the concentration of the respective element in the surface film from the size of the peak (by calculating the integral over the peak while subtracting the base line).

It is, in particular, difficult to detect concentrations of light elements as their fluorescence radiation only has a low energy. To improve the resolution in this element range, on the one hand, a low-energy X-ray tube 1 can be used which has an anode material with a low cardinal number Z. Chromium, molybdenum, silver and tungsten can be used as materials for the anode. A second measure is to arrange the X-ray tube, the monochromator, the sample table and the transducer in a vacuum housing. In this way, the absorption of the X-ray radiation by air can be avoided. In the arrangement shown in FIG. 1, it is therefore of advantage to make the housing 3 as a vacuum housing and to evacuate it. A third measure is to reduce the absorption through the measuring windows provided either in the transducer or in each individual DRIFT detector. It is of advantage to provide a window with a thickness of less than 2 $\mu$m instead of the conventional beryllium window. It is possible also to determine the concentrations of light elements reliably by the above-mentioned three measures.

Figure 4:
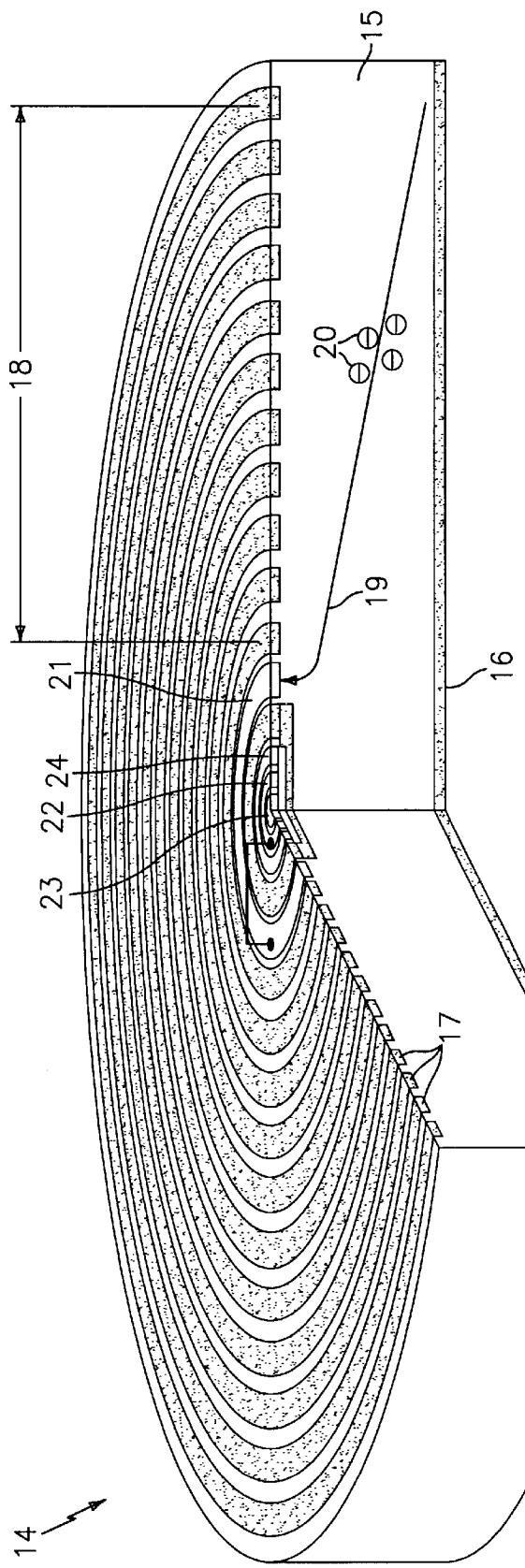
FIG. 4 shows a schematic representation of a DRIFT detector and the electrical field extension in the DRIFT detector.

In FIG. 4, the DRIFT detector 14 used is shown schematically. The detector 14 consists of a plate of n-doped silicon to whose one side a cathode 16 made of p-doped silicon is applied. On the opposite side of the plate, concentric annular electrodes 17 are applied which also consist of p-doped silicone. While the cathode 16 is held at a certain potential, the different annular electrodes 17 are at different voltage levels. For example, there is a voltage difference 18 between the two annular electrodes shown separately in FIG. 4.

An electrical field with a radially extending component is created in the detector interior 15 due to the voltage gradients 19 present between the two sides of the detector 14 in the radial direction of the plate. When charge carriers 20, that is electrons and holes, are generated by an incident X-ray quantum, the electrons created are accelerated in the direction of the annular anode 21 by the radial component of the electrical field.

A current surge proportional to the number of charge carriers generated can be measured between the cathode 16 and the annular anode 21. The main advantage of the DRIFT detector described is that the capacitance formed by the anode and cathode is a great deal smaller than with prior detector constructions, because the area covered by the annular electrode 21 can be made substantially smaller than the detector itself. In this way, the charge created can be determined very fast on the one hand and very precisely on the other.

The signal applied between the anode and the cathode is fed to a multi-channel counter, which then supplies the desired energy spectrum, after corresponding pulse amplification. It is of advantage to integrate the first transistor of the amplification stage directly to the upper side of the detector to allow the sensitive connection between the annular anode 21 and the gate input of the first field-effect transistor of the amplifier circuit to be made as short as possible. This is shown in FIG. 4. The annular electrode 21 is connected to the gate 22 of an FET integrated in the detector. The potential applied to the gate 22 can switch the source drain path (23, 24). The signal/noise ratio can be substantially improved by this measure.

Figure 5:
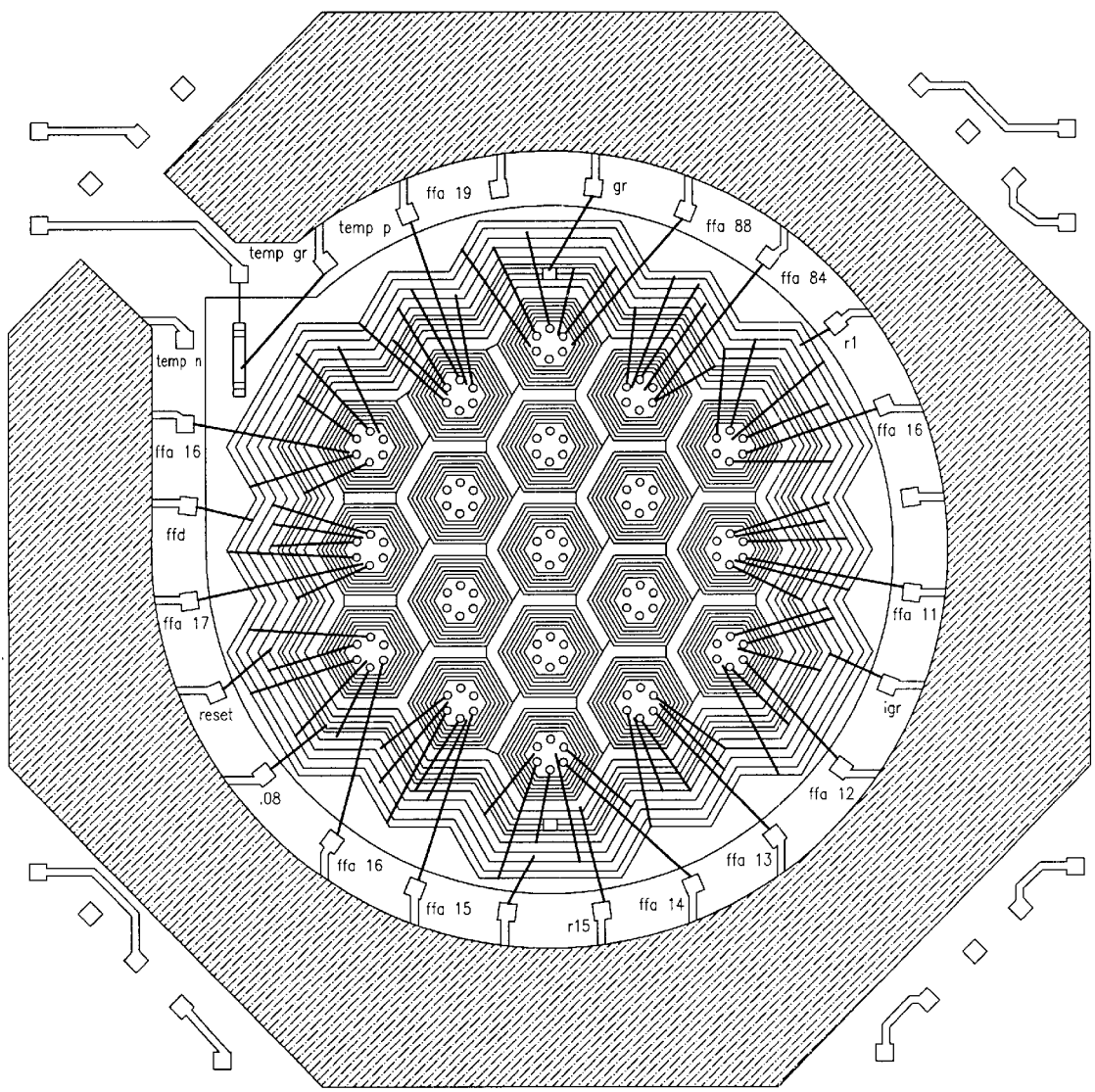
FIG. 5 shows the layout of an array of DRIFT detectors.

In FIG. 5, an array of DRIFT detectors is represented, with each individual detector showing the structure shown in FIG. 4. However, the annular electrodes are not circular, but hexagonal, whereby a characteristic honeycomb structure results. A high-sensitivity resolution measurement of the X-ray fluorescence of the sample can be made with the aid of such an array of DRIFT detectors. The topical concentration of various elements in the sample surface can be determined from the energy spectrums recorded. In this way, it is possible to present the distribution of a certain element on the surface measured in graphic form. It is of interest, in particular, in the measurement of foreign atom concentrations of wafers, to know at which point of the wafer surface contaminations are present as the diagnosis of the cause for the contaminations is made easier in this way.

It is to be expected that pulse amplification and evaluation electronics will be available as integrated circuits in the foreseeable future so that an analysis of the data generated by the many DRIFT detectors of the array will be possible with a reasonable effort.

Figure 6:
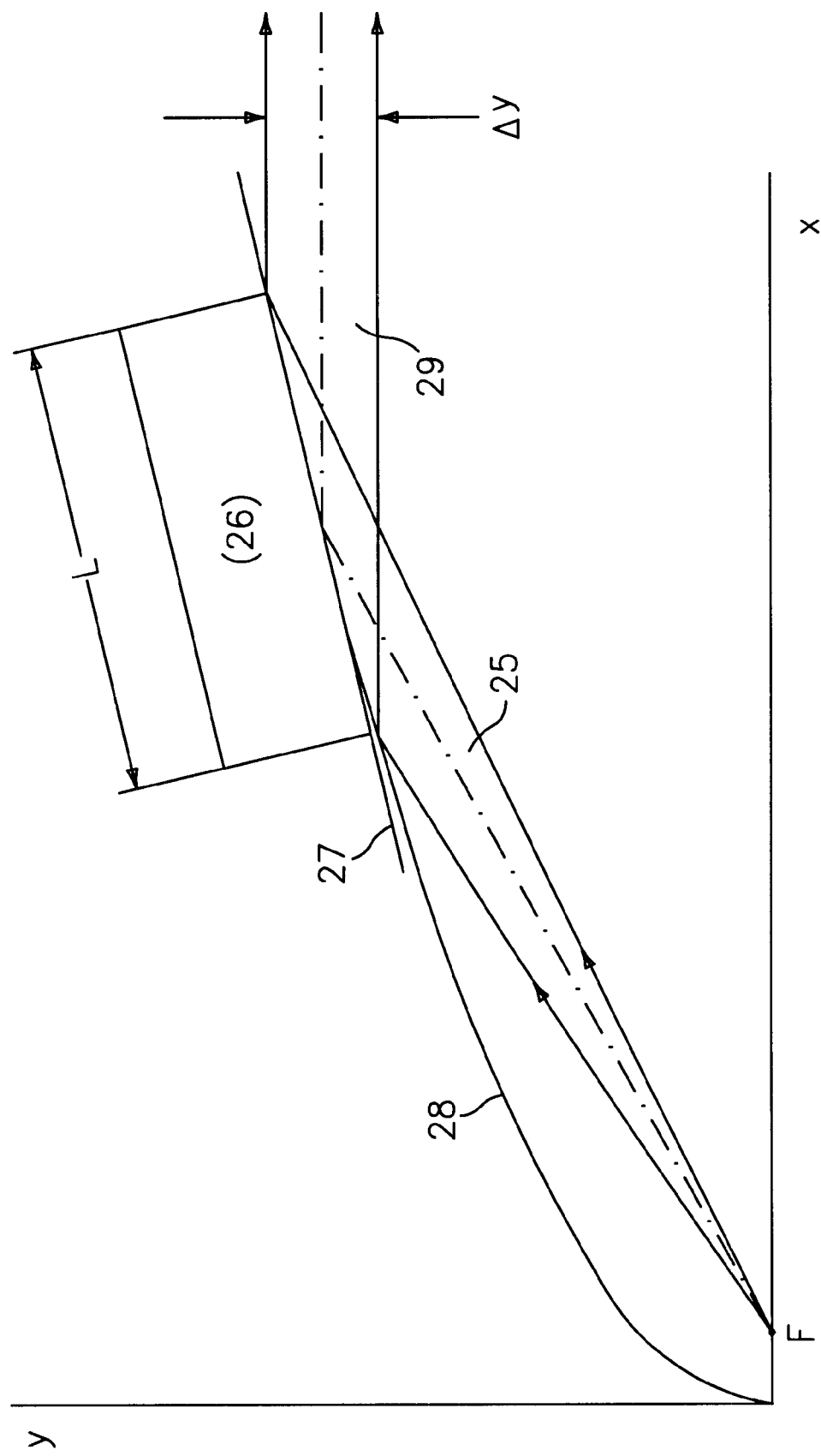
FIG. 6 shows an apparatus to generate a parallel X-ray using parabolically arranged Bragg reflectors.

The use of a wide-area detector requires an excitation X-ray with a large diameter which occurs at a low angle of incidence on the sample. In FIG. 6, a possibility to generate such an X-ray is shown. The divergent X-ray 25 emitted by an X-ray tube here is incident to a Bragg reflector 26 whose surface is arranged tangentially (27) to a parallel path 28. As with a parabolic projector, the Bragg reflector 26, which can be made either as a multi-layer generator or as a crystal, generates a parallel beam 29 with a diameter y which can be used to excite the sample.

Figure 7:
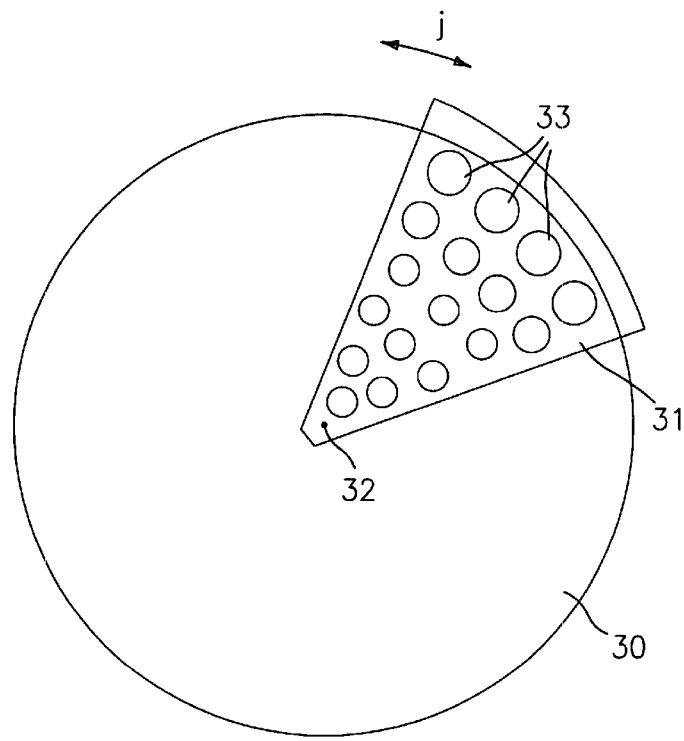
FIG. 7 shows an embodiment of an array of DRIFT detectors especially suited for wafer analysis, wherein the circular sector-shaped detector array can be rotated over the whole wafers.

In FIG. 7, a particularly favorable geometrical arrangement for the high-sensitive resolution measurement of foreign atom concentrations on a wafer surface is shown. For this purpose, a circular sector-shaped array 31 of DRIFT detectors 33 is provided. To record the high-sensitive resolution fluorescence, the wafer surface in the surface region covered by the array 31 is excited by an X-ray incident in parallel. The fluorescence spectrum can then be recorded by the DRIFT detectors 33. After the recording of the fluorescence spectrum in the sector covered, the wafer 30 is turned further around the center point 32 relative to the array 31.

Figure 8:
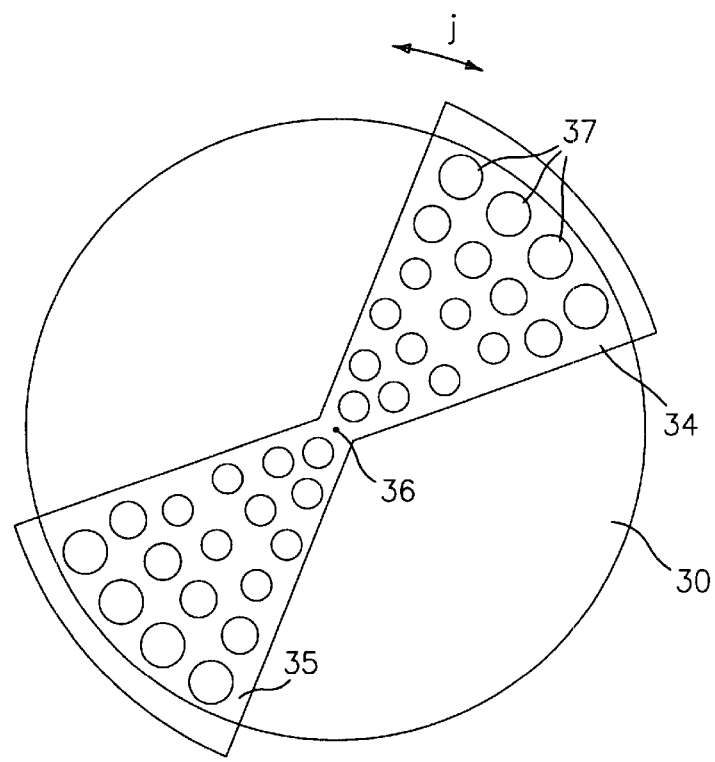
FIG. 8 shows an embodiment and an array of DRIFT detectors comprising two fixedly connected circular sector-shaped arrays.

The detector array shown in FIG. 8 comprises two fixedly connected circular sector-shaped arrays 34 and 35 of DRIFT detectors 37. The two circle sectors are arranged diametrically opposite one another and can be turned (arrow j) around the axis of rotation 36 relative to the wafer 30 to be measured, with either the wafer or the detector array being moved. To record the high-sensitive resolution fluorescence, the wafer surface is excited by an X-ray of parallel incidence in the region covered by the arrays 34 and 35; subsequently, the fluorescence spectrum is recorded by the DRIFT detectors 37. After the recording of the fluorescence spectrum, the detector array is turned further by a certain angle.

What is claimed is:

1. An apparatus for total reflection X-ray fluorescence analysis (TRFA) in which the smooth planar surface of a sample or thin film on a sample is excited by the incident X-ray radiation and the emitted X-ray fluorescence radiation is detected spectrally and which comprises a radiation source, a monochromator and a transducer, wherein the transducer comprises at least one DRIFT detector, with an electrical field, which has a radial component, being capable of generation in each DRIFT detector by means of an electrode array of electrodes at different voltage levels, with charge carriers created being able to be accelerated towards a low-capacitance collecting electrode by the radial component of the electrical field.

2. An apparatus for total reflection X-ray fluorescence analysis in accordance with claim 1, wherein the electrode array comprises a plurality of concentrically arranged annular electrodes at different voltage levels.

3. An apparatus for total reflection X-ray fluorescence analysis in accordance with claim 1, wherein a first transistor of a pulse amplification stage is integrated in the collecting electrode.

4. An apparatus for total reflection X-ray fluorescence analysis in accordance with claim 1, wherein the DRIFT detector can be cooled by a Peltier cooler element.

5. An apparatus for total reflection X-ray fluorescence analysis in accordance with claim 1, wherein the radiation source, the monochromator and the transducer are arranged in a vacuum housing.

6. An apparatus for total reflection X-ray fluorescence analysis in accordance with claim 1, wherein the transducer has a thin window with a thickness of less than 2 $\mu$m as the measurement window.

7. An apparatus for total reflection X-ray fluorescence analysis in accordance with claim 1, wherein the radiation source comprises a low-energy X-ray tube.

8. An apparatus for total reflection X-ray fluorescence analysis in accordance with claim 1, wherein a sample table is arranged opposite the transducer to accommodate a sample, with said sample table being made longitudinally displaceable preferably in the z direction and in the x direction, rotatable around its middle axis and pivotable in a circular segment guide.

9. An apparatus for total reflection X-ray fluorescence analysis in accordance with claim 8, wherein the sample table can be travelled by means of very finely resolving step motors.

10. An apparatus for total reflection X-ray fluorescence analysis in accordance with claim 8, wherein the sample table has a suction plate as the accommodating plate in which a plurality of pins travellable over their upper plane are integrated.

11. An apparatus for total reflection X-ray fluorescence analysis in accordance with claim 1, wherein the transducer is travellable in the z direction.

12. An apparatus for total reflection X-ray fluorescence analysis in accordance with claim 1, wherein a scattered radiation diaphragm is situated in front of the transducer.

13. An apparatus for total reflection X-ray fluorescence analysis in accordance with claim 1, wherein the scattered radiation diaphragm can be travelled in the z direction.

14. An apparatus for total reflection X-ray fluorescence analysis in accordance with claim 1, wherein the excitation of the sample is made by means of an incident parallel X-ray which is generated with the aid of Bragg reflectors arranged parabolically which reflect the X-ray radiation emitted by an X-ray tube.

15. An apparatus for total reflection X-ray fluorescence analysis in accordance with claim 1, wherein the transducer comprises a detector array of a plurality of DRIFT detectors, which allows a high-sensitive resolution recording of the X-ray fluorescence radiation of the sample.

16. An apparatus for total reflection X-ray fluorescence analysis in accordance with claim 15, wherein the detector array can be operated in a first and in a second mode, with the X-ray fluorescence radiation of the sample being measured in high-sensitive resolution in the first mode, and with the sum spectrum of the X-ray fluorescence spectrums supplied from the individual detectors being determined in the second mode.

17. An apparatus for total reflection X-ray fluorescence analysis in accordance with claim 15, wherein the sample and the transducer are movable relative to one another in the x,y direction.

18. An apparatus for total reflection X-ray fluorescence analysis in accordance with claim 15, wherein the detector array is made in the form of at least one circular sector, with the detector array and the sample being pivoted relative to one another with respect to an axis extending through the sector peak.

19. An apparatus for total reflection X-ray fluorescence analysis in accordance with claim 15, wherein the detector array covers an area which is greater than the area of the sample.

20. Use of an apparatus in accordance with any of claim 1 to determine foreign atom concentrations on wafer surfaces.

21. The apparatus of claim 1, comprising an array of DRIFT detectors arranged to form a honeycomb structure with each said DRIFT detector being hexagonal.

22. The apparatus of claim 1, wherein said DRIFT detector (14) comprises
  a plate of n-doped silicon,
  a cathode (16) formed of p-doped silicon being applied to a side of said plate of n-doped silicon,
  on an opposite side of said plate of said n-doped silicon from said cathode (16), concentric annular electrodes (17) being applied and also formed of p-doped silicon,
  said cathode (16) and annular electrodes (17) being structured and arranged with respect to one another such that when said cathode (16) is maintained at a certain potential, said annular electrodes (17) are each at different voltage levels from one another with voltage difference being formed therebetween, and an electrical field having a radially extending component being created within an interior (15) of said DRIFT detector (14) due to voltage gradients (19) present between the two sides of said detector (14) in a radial direction of the plate, said charge carriers (20) generated by incident X-ray quantum, being accelerated in a direction of an innermost annular anode (21) by said radial component of said electrical field, and a gate (22) of an FET integrated in said DRIFT detector (14) being connected to said innermost annular anode (21) such that potential applied to said gate (22) can switch a source drain path (23, 24).

23. The apparatus of claim 21, wherein said DRIFT detector (14) comprises a plate of n-doped silicon, a cathode (16) formed of p-doped silicon being applied to a side of said plate of n-doped silicon, on an opposite side of said plate of said n-doped silicon from said cathode (16), concentric annular electrodes (17) being applied and also formed of p-doped silicon, said cathode (16) and annular electrodes (17) being structured and arranged with respect to one another such that when said cathode (16) is maintained at a certain potential, said annular electrodes (17) are each at different voltage levels from one another with voltage difference being formed therebetween; and an electrical field having a radially extending component being created within an interior (15) of said DRIFT detector (14) due to voltage gradients (19) present between the two sides of said detector (14) in a radial direction of the plate, said charge carriers (20) generated by incident X-ray quantum, being accelerated in a direction of an inner most annular anode (21) by said radial component of said electrical field; and a gate (22) of an FET integrated in said DRIFT detector (14) being connected to said innermost annular anode (21) such that potential applied to said gate (22) can switch a source drain path (23, 24).

24. The apparatus of claim 22, wherein said DRIFT detector (14) is circular.

25. A method for the high-sensitive resolution measurement of foreign atom concentrations on the surface of a wafer by means of total reflection X-ray fluorescence analysis, wherein the measurement is performed while using a detector array comprising a plurality of detectors and comprises the following steps:

a) generation of a relative movement between the detector array and the sample to be measured;

b) recording of the respective topical X-ray fluorescence spectrums;

c) determining of the respective topical foreign atom concentrations from the X-ray fluorescence spectrums recorded there in each case.

26. A method for the high-sensitive resolution measurement of foreign atom concentrations in accordance with claim 25, wherein the detector array comprises a plurality of DRIFT detectors, with an electrical field being able to be generated in each DRIFT detector by means of an electrode array of electrodes at different voltage levels, said field having a radial component, with charge carriers created being able to be accelerated towards a low-capacitance collecting electrode by the radial component of the electrical field.

27. A method for the high-sensitive resolution measurement of foreign atom concentrations on the surface of a wafer by means of total reflection X-ray fluorescence analysis, wherein the measurement is performed while using a detector array comprising a plurality of detectors and comprises the following steps:

a) generation of a relative movement between the detector array and the sample to be measured;

b) recording of the respective topical X-ray fluorescence spectrums;

c) summing of the topical X-ray fluorescence spectrums;

d) determining of the mean topical foreign atom concentrations from the sum spectrum obtained in step c).

28. A method for the measurement of the mean foreign atom concentrations in accordance with claim 27, wherein the detector array comprises a plurality of DRIFT detectors, with an electrical field being able to be generated in each DRIFT detector by means of an electrode array of electrodes at different voltage levels, said field having a radial component, with charge carriers created being able to be accelerated towards a low-capacitance collecting electrode by the radial component of the electrical field.

* * * * *